United States Patent [19]

Schomburg et al.

[11] Patent Number: 4,972,729

[45] Date of Patent: * Nov. 27, 1990

[54] DEVICE FOR SPLIT AND SPLITLESS SAMPLING ONTO CAPILLARY COLUMNS USING A SYRINGE

[75] Inventors: Gerhard Schomburg; Ulrich Häusig, both of Mülheim/Ruhr, Fed. Rep. of Germany

[73] Assignee: Studiengesellschaft Kohle mbH, Mulheim/Ruhr, Fed. Rep. of Germany

[ * ] Notice: The portion of the term of this patent subsequent to Jan. 23, 2007 has been disclaimed.

[21] Appl. No.: 391,341

[22] Filed: Aug. 9, 1989

Related U.S. Application Data

[60] Division of Ser. No. 243,954, Sep. 13, 1988, abandoned, which is a continuation of Ser. No. 146,909, Jan. 22, 1988, abandoned, which is a continuation of Ser. No. 935,473, Nov. 26, 1988, abandoned, which is a continuation of Ser. No. 777,978, Sep. 19, 1985, abandoned.

[30] Foreign Application Priority Data

Sep. 26, 1984 [DE] Fed. Rep. of Germany ....... 3435216

[51] Int. Cl.$^5$ .............................................. G01N 1/00
[52] U.S. Cl. .................. 73/864.86; 73/863.11
[58] Field of Search ...................... 73/863.11, 864.81, 864.84–864.87, 73/864.33

[56] References Cited

U.S. PATENT DOCUMENTS

| | | | |
|---|---|---|---|
| 3,401,565 | 9/1968 | Stoll et al. | 73/863.11 |
| 3,482,450 | 12/1969 | Harris, Jr. et al. | 73/864.86 |
| 3,798,973 | 3/1974 | Estey | 73/1 G |
| 4,269,608 | 5/1981 | Sisti et al. | 73/863.11 |
| 4,289,029 | 9/1981 | Sampson et al. | 73/863.11 |
| 4,300,393 | 11/1981 | Stearns | 73/863.11 |
| 4,357,836 | 11/1982 | Kokesh | 73/863.11 |
| 4,422,860 | 12/1983 | Feinstein | 55/197 |
| 4,474,588 | 10/1984 | Hinshaw, Jr. | 55/197 |

Primary Examiner—Robert Raevis
Attorney, Agent, or Firm—Sprung Horn Kramer & Woods

[57] ABSTRACT

An apparatus for conducting split sampling gas chromatography of a liquid sample comprising
 a vaporization chamber to receive a needle of a syringe,
 a first tube to receive the needle,
 a second tube directly adjacent the first tube and running substantially along the entire length of the first tube, the second tube accommodating a downward flow of cooling gas,
 a third tube surrounding the first tube and the second tube, thereby creating a annular space between the third tube and the first tube, the annular space accommodating an upward flow of gas exiting the third tube.

1 Claim, 2 Drawing Sheets

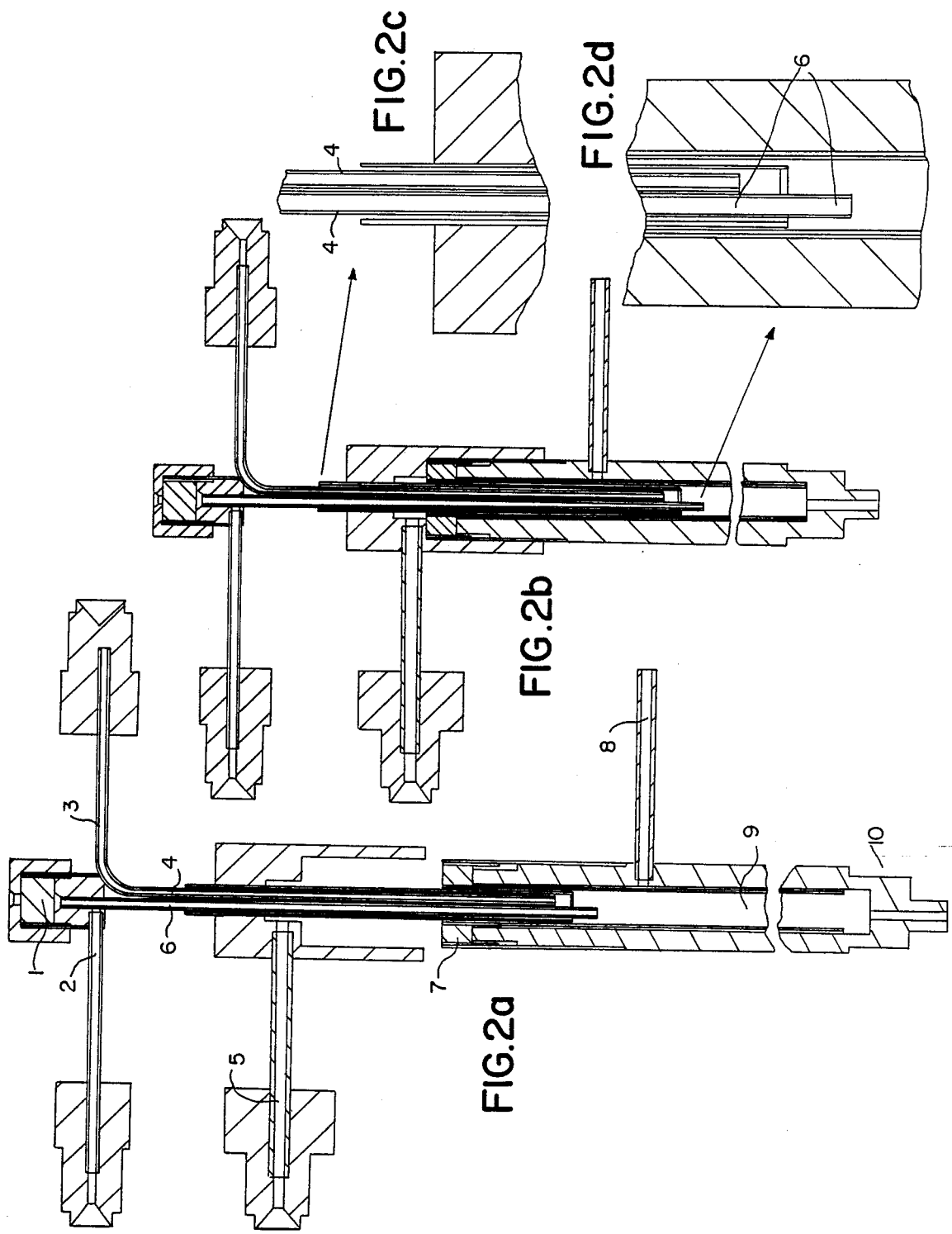

DEVICE FOR SPLIT AND SPLITLESS SAMPLING ONTO CAPILLARY COLUMNS USING A SYRINGE

This is a division of application Ser. No. 243,954, filed Sept. 13, 1988, now pending which is a continuation of application Ser. No. 146,909, filed Jan. 22, 1988, now abandoned, which is a continuation of Ser. No. 935, 473, filed Nov. 26, 1988, now abandoned, which is a continuation of Ser. No. 777,978, filed Sept. 19, 1985, now abandoned.

BACKGROUND OF THE INVENTION

1. Field of the Invention

The invention concerns a way of conducting split- and splitless sampling (with external vaporization) on capillary columns by syringe with improved precision and accuracy of quantitative analysis.

2. Background Information

For certain, especially, less diluted samples ranging widely in volatilities of the analytically significant components, the application of split sampling is the simplest technique for regulating the sample amount that is to enter capillary columns in order to avoid overloading. (D. H. Desty, A. Goldup, B. A. F. Whymann, J. Inst. Petroleum, 45 (1959) 287; I. Halasz, W. Schneider, Anal. Chem., 33 (1961) 987; L. Ettre, W. Averill, ANal, Chem., 33 (1961) 680; G. Schomburg, H. Husmann, H. Behlau, J. Chormatogr., 203 (1981) 179; K. Grob Jr., Proceed, 4th Int. Symp. Capillary Chromatogr. Hindelang 1981, p. 185;). The sampling volume or the sample amount which is actually entering the column can be varied in a double manner, either by the volume which is adjusted within the syringe cylinder or, over a wider range by the splitting ratio, i.e., the ratio between the splitting-flow of the carrier gas leaving the system, and that smaller part of the carrier-gas-flow that enters the column. Splitting ratios are usually varied within the range of 1:10–1:500.

For various instrumental reasons the method of split sampling onto capillary columns had been recognized in the past as insufficient and unreliable for the quantitative analysis of samples widely ranging in component volatilities. The application of this method therefore required elaborate additional calibration measurements in order to eliminate the systematical errors involved in the classical mode of execution of split sampling. The problems arising with split sampling at the quantitative GC-analysis using capillary columns will be discussed in more detail below. The subject of the invention to be described here, is a simple device to remove most of the sources of systematical errors arising at quantitative analysis.

Using the split sampling, mainly such samples are dosed into a GC-system, which are not highly diluted by a matrix solvent or such which must usually be diluted by a solvent in order for the cold "on-column"-technique to be applied for sampling. (G. Schomburg, H. Behlau, R. Dielmann, H. Husmann, F. Weeke, J. Chromatogr., 142 (1977) 87; K. Grob, K. Grob Jr., J. Chromatogr., 151 (1978) 311; K. Grob, HRC CC, 1 (1978) 263).

The procedure of split sampling can be described as follows: The sample volume is adjusted within a common syringe of 1–10 ~1 total volume; about 0.1–1.0 liters of the sample being dosed. The syringe needle is then introduced via the septum into the hot vaporization chamber of the injector. The sample is extruded from the syringe into the vaporization chamber by piston moving. The sample is vaporized and homogeneously mixed with the carrier gas, e.g., $CO_2$, and or nitrogen. Thereby droplet (aerosol) formation is prevented by a packing of deactivated glass or quartz wool. The vaporization temperature within the insert (200°–300° C.) must be adjusted according to the volatility of the less volatile sample constituents.

The mixture of carrier gas-sample vapour, is quickly transferred from the vaporization part of the insert into its split region by the high carrier-gas-flow, there, where the splitting takes place, according to the splitting ratio (ratio of splitting flow to column flow of carrier gas). A minor part of the sample thus enters the column, the major part of the sample leaves the system via the split exit.

The column itself (but not the column inlet which protrudes into the heated vaporization chamber) can be maintained at temperatures which are usually lower than the injector temperature is during the sample transfer into the column. The column temperatures may also be low, if temperature programming is to be applied for the separation. The injector temperature must be high, if components of low volatility are, however, contained within the sample.

The criteria for optimized split sampling are:

(a) The absolute sample amount (measured by the total of peak areas) which actually enters the column, must be well defined and reproducible. It must also correspond to the adjusted syringe volume as well as to the splitting ratio. Low standard deviations (5%) of the absolute amounts of the significant sample components, are desirable. In trace analysis such standard deviations may be sufficiently low to avoid the application of the internal standard method for quantitation.

(b) The relative amounts of the sample components which are measured by relative peak areas must not, when on its way from the syringe into the column, be changed by "discrimination" of either volatile or less volatile components. (G. Schomburg, H. Husmann, H. Behlau, J. Chromatogr., 203 (1981) 179). This means that the composition of the original sample may not differ from the composition of that part of the sample that enters the column. The relative peak areas which correspond to the relative concentrations of the constituents must also be reproducible by means of repetitive measurements. The relative standard deviation should be as low as 1% and less for quantitative analyses. Low standard deviations of relative peak areas or amounts of components respectively and even lower systematical errors (i. e., high accuracy) are absolutely necessary to achieve. These rigid requirements were not met by application of the hitherto known devices for split injection onto capillary columns.

(c) The achievement of the optimum separation efficiency of the column may not be prevented by the sampling procedure, especially not with isothermal column operation, because peak focussing (thermal or by solvent effects) is difficult or impossible to attain then.

Sources of errors at quantitative analyses using split sampling:

The syringe needle, which is filled with the liquid sample, must be introduced into the hot injector chamber, which must be kept at even higher temperature, if components of very low volatility are contained in the sample, which otherwise would remain unvaporized within the injector. Temperatures between 200° and 300° C. are usually necessary. From the needle a selective vaporization of the more volatile sample constituents into the carrier gas arises towards the end of the extrusion of the liquid sample into the insert. The less volatile constituents of the sample remain within the syringe needle and are removed from the system during withdrawal of the syringe from the injector. (K. Grob Jr., H. P. Neucom, J. Chromatogr. 195 (1980) 64; G. Schomburg, Proceed. 4th Int. Symp. Capillary Chormatogr., Hindelang 1981 and A. 921). In this way, too many of the volatile components of the sample enter the column. The gas chromatogram obtained in this case appears as though discrimination of the low volatility components has occurred. A deviation from the true composition of the sample is observed. At the same time the standard deviations of the relative as well as the absolute peak areas, as obtained from the chromatograms, are high also. Before the extrusion of the liquid sample occurs, difficulties with selective vaporization of volatile components from the needle may also arise, because the sample is prematurely vaporized by heat transfer from the injector to the needle. Problems, especially, arise with samples which contain low boiling compounds or even dissolved gases. In this case the absolute sample amount that enters the injector, is falsified through formation of gas bubbles. The same can simply happen by thermal expansion of the liquid sample within the needle. It has previously been observed that such sampling errors are higher when hydrogen is the carrier gas, because the heat transfer onto the needle is much faster in this gas for reason of its high thermoconductivity. (G. Schomburg, H. Husmann, H. Behlau, J. Chromatogr., 203 (1981) 179). Further sources of error, which give rise to unreliable quantitative data, are related to the splitting process itself. For example: By the vaporized sample the viscosity of the carrier gas may be differently changed in the splitting or in the column flow. The effective splitting ratio may be different for the earlier and the later vaporized sample components.

Generally, errors at split sampling can be avoided, if the syringe needle is introduced and withdrawn as fast as possible. Moreover, the injector temperature should be as low as possible but considering the volatility of the constituents of lower volatility. (G. Schomburg, H. Husmann, H. Behlau, J. Chromatogr., 203 (1981) 179).

At the 6th Internat. Symp. Capillary Chromatogr., Riva del Garda, an automated split injector was presented by the Hewlett-Packard company, which is capable of very fast syringe manipulation in order to reduce the heat-up of the syringe needle and the related selective vaporization (according to the observations made by Schomburg, which are mentioned above). The provision of temperature decrease, within the insert, can generally not be applied, if the sample contains components of low volatility, which can only be volatilized and transferred into the column at higher temperatures.

The application of matrix solvents of higher boiling point and the avoidance of hydrogen as carrier gas can improve the situation but cannot completely exclude these sources of error.

The cooling of the whole injector, down to temperatures of 80°-100° C. prior to the introduction of the syringe needle and the extrusion of the liquid sample followed by fast heating of the entire injector, including both carrier-gas-flows, revealed, however, that discrimination of the more volatile sample components cannot be avoided, which is probably caused by inhomogeneous heating of the insert (carrier gas of the splitting flow) and of the column inlet (column flow).

SUMMARY OF THE INVENTION

All of the disadvantages mentioned can be avoided by the "cooled needle split sampling" in accordance with our invention. Therewith split sampling is performed through cooling of the needle at isothermal operation of the vaporization insert and especially, the splitting region.

DESCRIPTION OF THE DRAWINGS

The construction proposed and schemes of operation of this new type of device with which the split sampling errors are being avoided, as discussed above, are described in conjunction with the accompanying drawings, wherein:

FIGS. 2a, 2b, 2c and 2d are elevational views in cross-section of an apparatus according to the invention.

Figure 1:
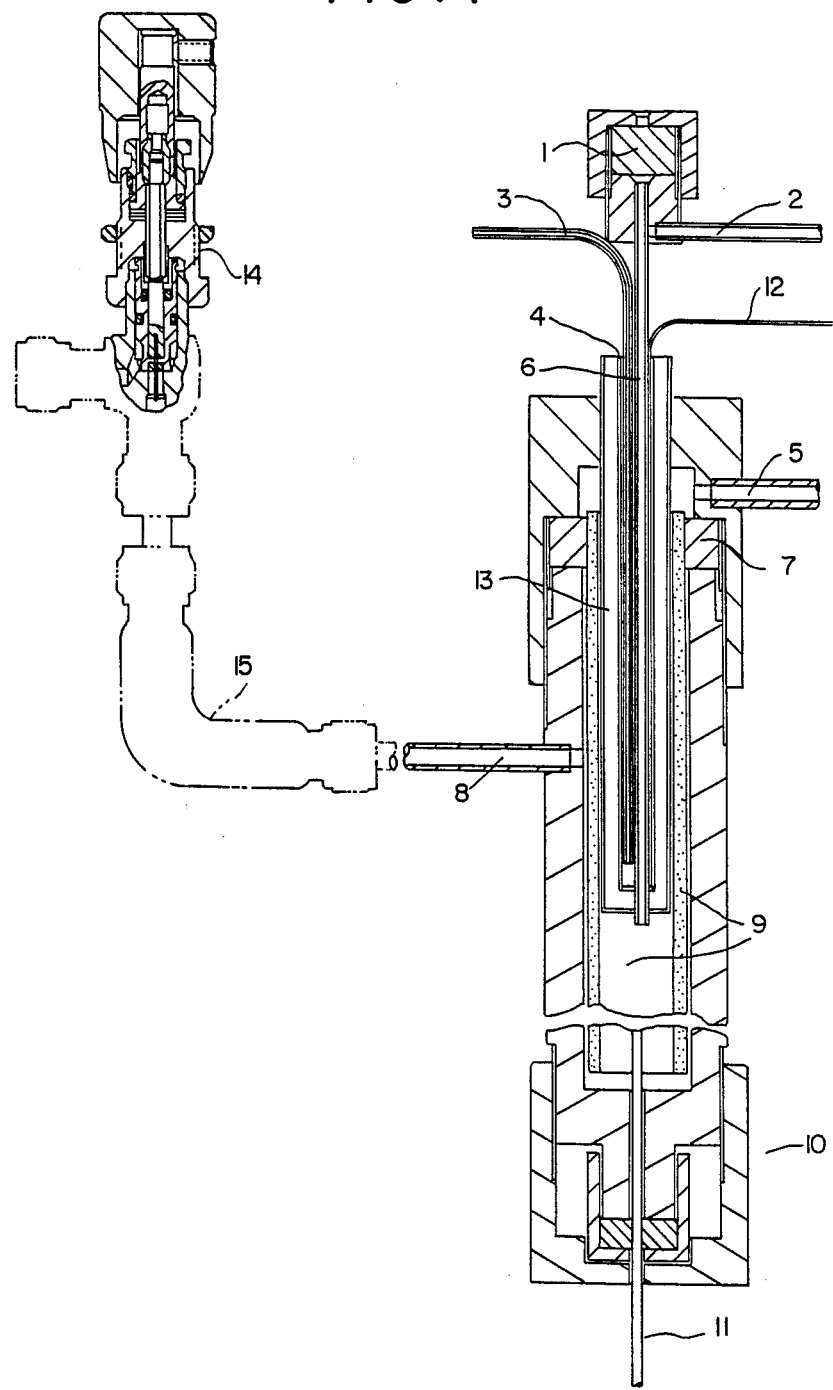
FIG. 1 is a longitudinal section through an apparatus in accordance with the invention.

Referring now more particularly to the drawings,

DETAILED DESCRIPTION OF THE INVENTION

The needle of the syringe is moved through the septum 1 and through the tube 6 so far that the needle tip just protrudes from the lower end of the cooling mantle into the vaporization chamber. The cooling medium enters the device through tube 3 cooling medium inlet tubs which leaves the lower end of the cooling medium inlet tube 3 and then flows upwards along the cooling mantle 6. The cooling medium leaves the cooling device at a cooling medium outlet 4 in FIG. 2 and cools the injector head 1 also. The tube 4 is closed at the lower end, preventing the cooling medium from entering the vaporization chamber 9. A temporary (short time) but, if desired, also a permanent cooling of the whole needle can be attained during the period of the needle introduction as long as the needle is kept within the injector.

FIG. 1 also depicts a capillary column connector 10, a capillary column 11, a thermocouple 12, insulation 13, a needle valve 14 and an adsorption tube 15.

Besides split sampling, needle cooling according to this invention is also suited to reduce the discrimination and other sampling errors arising from the wide volatility range of the sample with the known split less sampling method. The cooled needle split or splitless sampling can also be successfully applied to aqueous samples.

The temperature programmed operation of the whole injector (PTV or programmed temperature vaporization), as described above, is inferior to the instant CNS (cooled needle split sampling) technique, mainly, because of the more sophisticated construction and because of the splitting errors which cannot completely be suppressed with the PTV-technique caused by changes of the splitting ratio during the heating period. Discrimination of the more volatile components cannot be avoided. Superiority if established by comparing the data of the measurement series 4 and 5 (CNS) in Table 1 with the data of series 7 and 9 (cold "on-column" injection) in Table 2.

It finally must be mentioned that a partial cooling of the syringe needle (in its upper part) with only splitless sampling onto packed columns, was described by A. P. Schlunegger (J. Chromatogr., 27 (1967) 237). The objective in the work of this author was to achieve that defined amounts of blood samples could be dosed reproducibly. Splitting was not of interest for that work performed with packed column. Discrimination was also not being discussed. The author did not explicate of which kind the "dosage error" really was. It has not been defined so far, whether or not among the so-called "volatile" components a discrimination by volatility occurs also. Because of the splitless execution of the sampling onto packed columns, this point is not of major importance. Obviously, the author intended to achieve a defined ratio between the absolutely nonvolatile and the entire volatile constituents. Important was that the sampling volume of the serum, as adjusted in the syringe, corresponds properly to the measured amount of volatile components in total.

The application of the "cooled needle split" device in conformity with the invention and the results obtained with the test measurements in regard to the discrimination-free split sampling, are described as follows:

For these measurements one of the common test mixtures consisting of n-paraffins of a C-number range between 10–32 was used. n-heptane (b. p. 100° C.) was the matrix solvent. The volatilities of the test paraffins are characterized by the b. p. of the lowest hydrocarbon n-decane (174.2° C.) and of the highest hydrocarbon $C_{32}$ (474.7° C.). From 9 different series of test measurements using the new technique in comparison to those already known, the absolute and relative peak area data for each single component were determined and normalized to 100%. The true composition of the mixture was known from weighing, but was also determined by application of other sampling techniques well known as reliable and discrimination-free, such as the "cold on-column" technique. Therewith, the precision was also determined from at least 5 measurements for both the absolute and the normalized (relative) peak area data. The peak areas obtained with flame ionization detection are directly proportional to the weights of the test paraffins. Therefore, calibration factors of the conversion of areas into weight of paraffin need not be applied to paraffins. Table 1 contains the data originating from 5 different series for which split sampling, using different types of devices, were used or operated at different parameters.

Series 1

A standard split injector with a glasswool packed insert was used in a Varian 3700 GC with FID. The same injector was also used for the series 2–5. The temperature of the splitter was 260° C., the splitting ratio 1:44. Selective vaporization from the needle produces errors in the quantitative data, fi the injection is performed too slowly, if the splitter temperature is too high, if the solvent is too volatile, and if the carrier gas is hydrogen, etc (G. Schomburg, H. Husmann, R. Rittmann, J. Chromatogr. 204 (1981) 85). Strong discrimination of the high C-number paraffins is observed because of selective vaporization of the volatile hydrocarbons.

Peak area $C_{10}$: 14.2 (instead of 8.33)%
Peak area $C_{32}$: 6.4 (instead of 8.33)%

Series 2

The additional device which is in conformity with the invention that allows to keep the syringe needle cold during the dosing procedure, was primarily tested without a flow of the cooling medium. As with Series 1 much too high areas were found for the less volatile paraffins. The splitting ratio in this series was 1:60.

Peak area $C_{10}$: 9.8 (instead of 8.33)%
Peak area $C_{32}$: 7.3 (instead of 8.33)%

Series 3a

The same configuration as with series 2 and the same parameters of operation were selected. But now, during the injection, the needle was cooled by nitrogen or air flow of ambient temperature. The splitting ratio was 1:20. Under these conditions, with a weak cooling of the needle, the discrimination already vanished. All peak area data are close to 8%.

Peak area $C_{10}$: 8.57 (instead of 8.33)%
Peak area $C_{32}$: 8.13 (instead of 8.33)%

Series 3b

The same procedure as with series 3a was applied, the splitting ratio was increased to 1:55, however. The cooling medium was nitrogen at ambient temperature.

Series 4

The device and the parameters of operation were not changed, but the needle cooling was carried out with cold $CO_2$ originating from the head space of a $CO_2$ cylinder.

Peak area $C_{10}$: 8.19 (instead of 8.33)%
Peak area $C_{32}$: 8.63 (instead of 8.33)%

Series 5

Now the cooling was performed with cold $CO_2$ from the bottom of the $CO_2$ cylinder. No difference of the data was observed in comparison to the data of Series 1.

In all cases the standard deviations of the normalized peak area data were on average as low as 1% and below, provided needle cooling was applied using the CNS- technique. The absolute peak area could be reproduced with a relative standard deviation of less than 5%. These data were also directly proportional to variations of the splitting ratio. In this manner the sample load of the column can be varied by changing the splitting ratio without discrimination errors.

Even with the best measurements small deviations from the true values are still observed but are not of importance in practice. These deviations are so small that the discrimination effect can be recognized reliably, however.

Comparison of data obtained with CNS to such obtained with cold "on column" injection:

In Table 2 all data are given that were obtained with the same sample. However, for certain series, the sample had to be further diluted by the same solvent (n-heptane) in order to apply the on-column technique.

Series 6

The inverse cup on-column sampling technique (G. Schomburg et al., J. Chromatogr., 142 (1977) 87) was applied. The data obtained are in agreement with those obtained by the CNS technique. Considerable discrimination was not observed. The relative standard deviations are smaller than 1% on average.

Peak area $C_{10}$: 7.95 (instead of 8.33)%
Peak area $C_{32}$: 8.74 (instead of 8.33)%

Series 7

The "on-column" injection was executed by using an SGE device originating from the SGE company (D-6108, Weiterstadt, GFR). The data obtained was similar to that with the CNS technique. The relative standard deviations were below 1% on average.

Peak area $C_{10}$: 8.11 (instead of 8.33)%
Peak area $C_{32}$: 8.75 (instead of 8.33)%

All deviations from the theoretical value (8.33%) larger than 0.3% are probably caused by other, but much less important systematical errors.

Series 8

The "on-column" injection was executed using a device originating from the Chrompak Company, Middelburg, The Netherlands. A small discrimination of the more volatile hydrocarbons was observed which may be caused by a temperature gradient within the injector. The isolation between the column oven and the injector may have been imperfect.

Peak area $C_{10}$: 7.72 (instead of 8.33)%
Peak area $C_{32}$: 8.76 (instead of 8.33)%

Series 9

The "on-column" injection was executed using a device originating from the Carlo Erba Company, Milano, Italy. This injector was equipped with the so-called secondary cooling, at which the column inlet can be cooled additionally. The data obtained are in good agreement with the CNS data obtained in Series 4 and 5 of Table 1 and prove that samples ranging widely in component volatilities can be introduced into hot splitters without considerable discrimination. Moreover the peak areas obtained (column loads) are directly proportional to the splitting ratio.

Peak area $C_{10}$: 8.18 (instead of 8.33)%
Peak area $C_{32}$: 8.72 (instead of 8.33)%

TABLE 1

| | DISCRIMINATION TEST MEASUREMENTS USING COOLED NEEDLE SPLIT SAMPLING - CNS | | | | | | | | | | | | |
|---|---|---|---|---|---|---|---|---|---|---|---|---|---|
| | | $C_{10}$ | $C_{12}$ | $C_{14}$ | $C_{16}$ | $C_{18}$ | $C_{20}$ | $C_{22}$ | $C_{24}$ | $C_{26}$ | $C_{28}$ | $C_{30}$ | $C_{32}$ |
| Series 1 | | | | | | | | | | | | | |
| Vorion 3700 hot split (260° C.) Split: 1:44 | area % | 14.20 | 13.12 | 11.03 | 9.19 | 7.75 | 6.83 | 6.53 | 6.14 | 6.12 | 6.28 | 6.36 | 6.44 |
| | RSD (rel. areas) | 2.07 | 1.87 | 1.68 | 1.40 | 0.63 | 1.14 | 1.73 | 2.18 | 2.37 | 2.38 | 2.21 | 2.18 |
| Series 2 | | | | | | | | | | | | | |
| Vorion 3700 CNS without cooling Split: 1:60 | area % | 9.77 | 9.45 | 8.61 | 8.20 | 8.05 | 7.98 | 8.36 | 8.09 | 8.12 | 8.17 | 7.89 | 7.31 |
| Series 3a | | | | | | | | | | | | | |
| Vorion 3700 CNS with air cooling Split: 1:20 | area % | 8.57 | 8.66 | 8.43 | 8.29 | 8.16 | 8.17 | 8.53 | 8.22 | 8.25 | 8.34 | 8.25 | 8.13 |
| | RSD (rel. areas) | 0.82 | 0.48 | 0.63 | 0.72 | 0.42 | 0.24 | 0.43 | 0.50 | 0.50 | 0.50 | 0.79 | 1.47 |
| | RSD (abs. areas) | 5.74 | 6.06 | 6.27 | 6.29 | 6.13 | 5.90 | 6.70 | 5.44 | 5.45 | 5.45 | 5.68 | 6.37 |
| Series 3b | | | | | | | | | | | | | |
| Vorion 3700 CNS with air cooling Split: 1:55 | area % | 8.30 | 8.37 | 8.19 | 8.23 | 8.29 | 8.36 | 8.77 | 8.45 | 8.48 | 8.45 | 8.15 | 7.94 |
| | RSD (rel. areas) | 0.51 | 0.66 | 0.75 | 0.59 | 0.80 | 1.35 | 1.19 | 1.11 | 1.31 | 1.42 | 2.55 | 3.00 |
| | RSD (abs. areas) | 4.74 | 4.79 | 4.96 | 4.76 | 4.32 | 3.88 | 3.97 | 4.25 | 4.72 | 5.79 | 7.12 | 7.43 |
| Series 4 | | | | | | | | | | | | | |
| Vorion 3700 CNS with $CO_2$ (gas) Split: 1:44 | area % | 8.19 | 8.31 | 8.14 | 8.12 | 8.14 | 8.20 | 8.52 | 8.31 | 8.35 | 8.51 | 8.56 | 8.63 |
| | RSD (rel. areas) | 0.91 | 0.54 | 0.70 | 0.61 | 0.45 | 0.42 | 0.24 | 0.25 | 0.52 | 0.44 | 0.59 | 0.51 |
| | RSD (abs. areas) | 1.85 | 2.56 | 3.10 | 2.98 | 2.78 | 2.41 | 2.48 | 2.50 | 2.78 | 2.85 | 3.01 | 3.03 |
| Series 5 | | | | | | | | | | | | | |
| Vorion 3700 CNS with $CO_2$(liquid) Split: 1:44 | area % | 8.21 | 8.35 | 8.15 | 8.18 | 8.19 | 8.19 | 8.48 | 8.26 | 8.31 | 8.49 | 8.54 | 8.63 |
| | RSD (rel. areas) | 0.85 | 0.52 | 0.49 | 0.52 | 0.62 | 0.33 | 0.28 | 0.34 | 0.26 | 0.25 | 0.24 | 0.41 |
| | RSD (abs. areas) | 3.46 | 3.31 | 3.10 | 2.56 | 2.51 | 2.97 | 3.00 | 2.97 | 2.93 | 2.67 | 2.66 | 2.56 |

TABLE 2

| | DISCRIMINATION TEST MEASUREMENTS USING COLD ON - COLUMN INJECTION | | | | | | | | | | | | |
|---|---|---|---|---|---|---|---|---|---|---|---|---|---|
| | | $C_{10}$ | $C_{12}$ | $C_{14}$ | $C_{16}$ | $C_{18}$ | $C_{20}$ | $C_{22}$ | $C_{24}$ | $C_{26}$ | $C_{28}$ | $C_{30}$ | $C_{32}$ |
| Series 6 | | | | | | | | | | | | | |
| Becker Packard 427 on-column (inversed cup) | area % | 7.95 | 8.07 | 8.08 | 8.16 | 8.20 | 8.25 | 8.68 | 8.32 | 8.37 | 8.54 | 8.64 | 8.74 |
| | RSD (rel. areas) | 0.56 | 0.49 | 0.32 | 0.31 | 0.08 | 0.18 | 0.16 | 0.20 | 0.23 | 0.23 | 0.26 | 0.24 |
| Series 7 | | | | | | | | | | | | | |
| Sichroma 1 on-column (SGE) | area % | 8.11 | 8.34 | 8.11 | 8.13 | 8.14 | 8.15 | 8.47 | 8.25 | 8.34 | 8.57 | 8.64 | 8.75 |
| Series 8 | | | | | | | | | | | | | |
| Carlo Erba 2900 on-column (Chrompack) | area % | 7.72 | 8.02 | 8.02 | 8.10 | 8.15 | 8.28 | 8.75 | 8.45 | 8.44 | 8.58 | 8.72 | 8.76 |
| | RSD (rel. areas) | 0.37 | 0.28 | 0.31 | 0.37 | 0.22 | 0.59 | 1.07 | 0.45 | 0.25 | 0.32 | 0.81 | 0.33 |

TABLE 2-continued

| | | \multicolumn{12}{c}{DISCRIMINATION TEST MEASUREMENTS USING COLD ON - COLUMN INJECTION} |
|---|---|---|---|---|---|---|---|---|---|---|---|---|---|
| | | $C_{10}$ | $C_{12}$ | $C_{14}$ | $C_{16}$ | $C_{18}$ | $C_{20}$ | $C_{22}$ | $C_{24}$ | $C_{26}$ | $C_{28}$ | $C_{30}$ | $C_{32}$ |
| Series 9 | | | | | | | | | | | | | |
| | area % | 8.18 | 8.26 | 8.21 | 8.29 | 8.44 | 8.53 | 8.31 | 8.24 | 8.26 | 8.42 | 8.42 | 8.42 |
| Carlo Erba 4180 on-column (Carlo Erba) | RSD (rel. areas) | 0.38 | 0.34 | 0.44 | 0.55 | 0.66 | 0.88 | 0.29 | 0.52 | 0.55 | 0.72 | 0.69 | 0.71 |

What is claimed is:

1. An apparatus for conducting split sampling gas chromatography of a liquid sample comprising
a vaporization chamber to receive a needle of a syringe,
a first tube to receive said needle,
a second tube directly adjacent said first tube and running substantially along the entire length of said first tube, said second tube accommodating a downward flow of cooling gas,
a third tube surrounding said first tube and said second tube, thereby creating a annular space between said third tube and said first tube, said third tube fluidly communicating with a capillary column, said annular space accommodating an upward flow of gas exiting the third tube.

* * * * *